United States Patent
Nordling

(10) Patent No.: US 6,319,374 B1
(45) Date of Patent: Nov. 20, 2001

(54) REPLACEABLE MEASURING ELECTRODE SYSTEM

(75) Inventor: Magnus Nordling, Vallingby (SE)

(73) Assignee: CLL Connectors & Cables AB, Knvista (SE)

( * ) Notice: Subject to any disclaimer, the term of this patent is extended or adjusted under 35 U.S.C. 154(b) by 0 days.

(21) Appl. No.: 09/674,718

(22) PCT Filed: Apr. 23, 1999

(86) PCT No.: PCT/SE99/00667

§ 371 Date: Nov. 6, 2000

§ 102(e) Date: Nov. 6, 2000

(87) PCT Pub. No.: WO99/57554

PCT Pub. Date: Nov. 11, 1999

(30) Foreign Application Priority Data

May 6, 1998 (SE) .................................................. 9801585

(51) Int. Cl.⁷ ..................................................... G01N 27/26

(52) U.S. Cl. ..................... 204/400; 204/280; 204/297 R; 204/212

(58) Field of Search ...................................... 204/400, 404, 204/405, 416, 403, 434, 435, 212, 199, 200, 201, 213, 214, 215, 216, 217, 218, 286, 297 R; 324/446–450

(56) References Cited

U.S. PATENT DOCUMENTS 4,889,608  12/1989  Eickmann ............................ 204/212

*Primary Examiner*—T. Tung
*Assistant Examiner*—Alex Noguerola
(74) *Attorney, Agent, or Firm*—Young & Thompson

(57) ABSTRACT

A measuring electrode system having a measuring body 2 (22) replaceably provided on a rotatable shaft (21). The rotating shaft is provided with a spring loaded contact pin (25, 26). When the measuring body is attached to the shaft the electrodes (16, 18) running through the measuring body will be brought in electrical connection with the contact pins.

7 Claims, 2 Drawing Sheets

REPLACEABLE MEASURING ELECTRODE SYSTEM

TECHNICAL FIELD OF THE INVENTION

The present invention relates to a measuring electrode system for use with a measuring device for electrochemical determination of the content of one or several chemical substances in a solution, and more specifically to a replaceable measuring body on a rotatable shaft adapted therefor.

TECHNICAL BACKGROUND

A conventional amperometric determination of chemical components (hereinafter referred to as "analytes") in a solution is performed by immersing a number of electrodes, typically three, in the analyte solution. During electrochemical measurements an electrolyte, such as an ion forming salt or any other ion forming compound which when dissolved increases the conductivity of the solution, is usually added to the analyte solution. The three electrodes are referred to as working electrode (WE), reference electrode (RE) and counter electrode (CE). At least one working electrode is required, but there is no restriction to the use of any number of additional working electrodes, if this is advantageous for a specific desired type of measurement.

The reference electrode is designed to maintain a constant and well-defined electrical potential. With respect to this potential a fixed electrical potential, negative or positive, is applied on the working electrode by means of an external electronic device, a potentiostat. If analytes in the electrolyte solution being exposed to this potential undergoes reaction at the working electrode, an electrical current will flow between the working electrode and the counter electrode. This current may be measured, and reflects the concentration of the analyte(s) in the solution, while the direction of the measured current flow depends on whether an oxidation or a reduction process is present at the working electrode.

Ideally, no current flows through the reference electrode of a triple electrode system as described above. In the simplest case, the current measured between the working electrode and the counter electrode is directly proportional to the analyte concentration. The chemical reactions occurring at the counter electrode are usually of no interest from a measuring point of view. Therefore, the counter electrode is often separated from the analyte solution and is placed in a separate receptacle in a liquid being electrically connected with the analyte solution via a porous sintered glass filter.

In a similar way, instead of a potentiometer a control equipment delivering a constant current can be used, whereby a resulting potential is measured across the working electrode.

Under certain conditions the reference electrode and the counter electrode may be combined. This is possible when the processes occurring at the counter electrode are reversible with regard to a component in the electrolyte, so that the rate of the electrochemical processes at the combined electrode is not current limiting for measuring an analyte at the working electrode.

A difficulty experienced during amperometric measurements is to achieve well-defined conditions in the solution at the boundary layer adjacent to the working electrode. Such well-defined conditions are of importance for obtaining reliable measurement results from which valid conclusions, such as determination of concentration, may be drawn. The rate at which processes occur at the working electrodes is regulated by the rate of electron transfer across the boundary layer between the analyte in the solution and the electrode, and/or by the rate of analyte transport through the solution to this boundary layer.

In order to achieve a well-defined transport of analyte towards the electrode the working electrode is rotated. Therefore, this is usually formed as a cylindrical body provided with one or several electrodes, usually working electrodes. In a typical embodiment, a central disk-shaped disk electrode and outside this an annular ring electrode, are positioned on the flat end surface whereby both these electrodes are working electrodes.

Such a configuration is called a rotating ring-disk electrode. In addition to working electrodes, reference and counter electrodes could be integrated in the rotatable body as well.

The U.S. Pat. No. 4,889,608 to G. Eickmann describes an electrode system including one electrode, wherein the electrode is disposed in a replaceable electrode fixture, which electrode fixture is mounted via an adapter on an elongated solid metal shaft, the shaft also acting as an electric conductor. When changing an electrode, the electrode fixture is dismounted to allow replacement of the electrode.

Replacement of an electrode according to U.S. Pat. No. 4,889,608 requires a special tool. Alternatively, the entire electrode fixture is replaced. However, the electrode fixture includes several components making it comparatively expensive. Furthermore, the electrode system is adapted for the case of a single electrode only.

Therefore, there is a need for a simplified replaceable electrode system for an arbitrary number of electrodes.

SUMMARY OF THE INVENTION

It is the object of the present invention, as it is defined in claim 1, to provide a measuring electrode system having an easily replaceable measuring body and allowing an arbitrary number of electrodes.

According to the invention, this object is achieved with a measuring body of a generally cylindrical shape and being impermeably connectable to a rotatable shaft of the measuring system, wherein the rotatable shaft is provided with spring urged contact pins, and wherein each contact pin during the attachment of the measuring body is brought into contact with an end of an electrode, which electrode is provided with a second end on the outside of the measuring body.

According to the invention, the measuring body can be manufactured very simply and without moving parts. In addition, it may be adapted to any number of contact pins by being provided with a corresponding number of electrodes.

BRIEF DESCRIPTION OF THE DRAWINGS

Illustrative embodiments of the invention are described in more detail below, with the embodiments being illustrated in the attached drawings wherein.

DETAILED DESCRIPTION OF EMBODIMENTS

Figure 1:
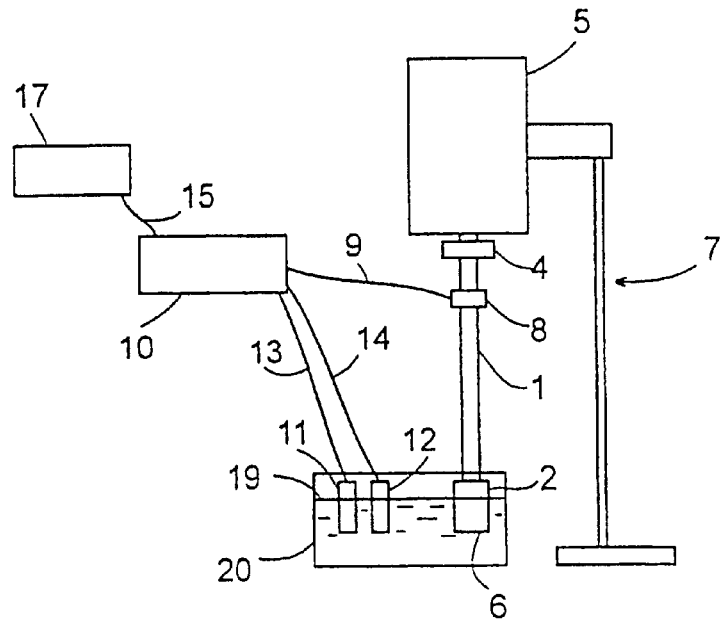
FIG. 1 is a schematical elevation view of a conventional measuring system.

First, a typical conventional measuring system shall be described in general terms as a background, with reference to the schematical illustration of FIG. 1. A typical conventional measuring system includes a measuring body 2 attached to a shaft 1. The shaft is, in its turn, connected to a motor 5 via a coupling device 4, in order to make the measuring body and the shaft rotatable. The motor is mounted onto a stand 7.

On the bottom surface of the measuring body 2 is disposed at least one working electrode 6. This working electrode is electrically connected to a potentiostat 10 via a lead (not shown) running through the shaft 1, a conventional collector connection 8 and a cable 9. A reference electrode 11 and a counter electrode 12 are connected to the potentiostat via the cables 13 and 14, respectively.

At use, the electrodes 6, 11 and 12 (the working electrode 6 being rotated) are immersed in an electrolyte and analyte solution 19 in a vessel 20. By providing a voltage across the working electrode a current is generated at the working electrode and is transferred to the potentiostat via the collector connection 8. The potentiostat outputs a measuring signal 15 based on the received current signal to a registering means 17. Power feeder cables have been omitted in FIG. 1 for reasons of clarity.

Figure 2:
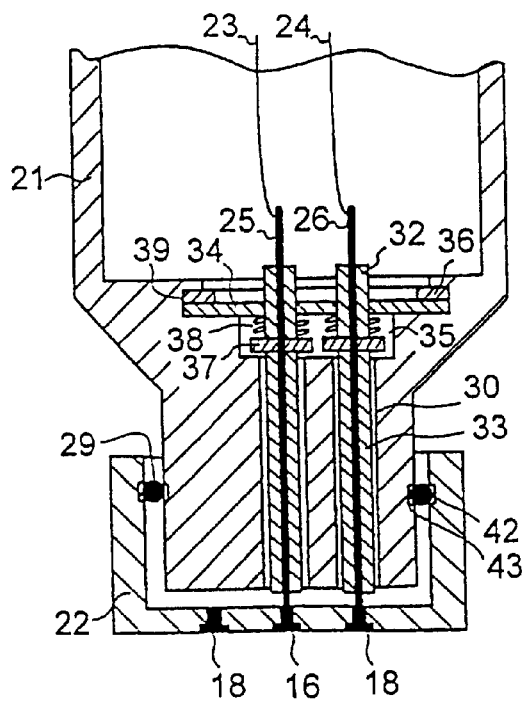
FIG. 2 is a cross sectional view of a first embodiment of a rotatable shaft and a replaceable measuring body according to the present invention.

The present invention relates to an improved design of a rotatable shaft and measuring body. A first embodiment of the invention is illustrated in FIG. 2, showing a cross sectional view of the lower section of a rotatable shaft 21 having a replaceable measuring body 22.

The rotatable shaft 21, which is formed of any suitable material withstanding the environment in which the measuring equipment is to operate, is hollow to house therein electronic leads 23, 24 to a collector connection (not shown in FIG. 2) for communication with the environment.

In the lower section of the rotatable shaft 21 are stiff contact pins 25, 26 disposed that are connected to the electrical leads 23, 24 by, for example, soldering. The number of contact pins corresponds to the number of electrodes 16, 18 for which the measuring equipment is adapted, two being shown in FIG. 2.

Each contact pin 25, 26 extend through an elongated bore 30, essentially in parallel with the central axis 21 of the shaft.

A shrinking tubing, partitioned into an upper portion 32 and a lower portion 33, is shrunk onto the connecting pin and serves as insulation with respect to the bottom shaft section but also as a stiffening means. In its upper end the lead, thus stiffened, extends with a clearance through a hole in a washer 34 provided in a groove 39 in a centrally disposed recess 35 in the bottom of the hollow interior of the rotatable shaft. The washer is made of a stiff, preferably electrically insulating material, such as polyamide, PA. The washer is locked in the groove with a conventional locking ring 36.

In a position below the washer 34, but above the bottom of the recess 35, is the upper shrinking tubing 32 separated from the lower shrinking tubing 33 by a sleeve 37. The sleeve has a wider diameter than the shrinking tubing so that, for each contact pin, one end of a compression spring 38 abuts against the upper sleeve end while the other end of the compression spring abuts against the washer 34. Thus, the compression spring will bias each contact pin, respectively, such that the pin always presses downwards. At the same time, each sleeve 37 is wider than each bore 34, respectively, thereby preventing the contact pins from being urged out of the shaft when the measuring body is removed.

The replaceable measuring body 22 adapted to the rotatable shaft 21 is formed from a material having suitable mechanical and chemical properties, such as polyamide, PA.

Figure 4:
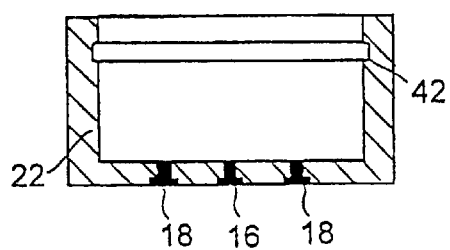
FIG. 4 is a separate cross sectional view of the measuring body shown in FIG. 2.
Figure 5:
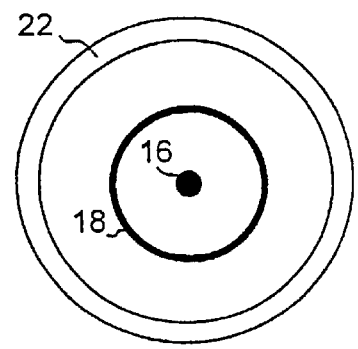
FIG. 5 is a top view of the measuring body according to FIG. 4.

The embodiment of the measuring body 22, which is shown in FIG. 2 and in more detail in FIG. 4 and 5, is formed as a hollow cylinder with a bottom held in its position on the rotatable shaft 21 by the clamping force of an O-ring 29. The O-ring is disposed in a groove 41, 42 in the rotatable shaft and in the inside of the measuring body, respectively, whereby the shape and the measures of the grooves are selected such that the measuring body can be detached and attached by hand and also such that the O-ring will act as a sealing.

Two electrodes 16, 18 are introduced through the bottom of the measuring body 22. One of the electrodes 18 has an annular shape and, thus, the measuring body will correspond to a ring-disk electrode. The electrodes are exposed at each side of the bottom of the measuring body such that one side of each electrode is exposed at the outside bottom surface of the measuring body to be brought into contact with the solution to be analyzed, while the other side of each contact pin is adapted to be brought into contact with its respective contact pin 25, 26 in the shaft.

By placing one of the contact pins 25 in the center of the rotatable shaft and a second contact pin 26 at a distance from the shaft center, said distance corresponding to the ring electrode 18 radius, the effect that the measuring body is mounted on the shaft with proper electrical connection regardless of the angular position of the measuring body is obtained.

When fastening the measuring body on the shaft, the contact pins are pressed into the shaft by the inner electrode surfaces of the measuring body, thereby providing good electrical contact by means of the reaction force from each compression spring, respectively.

Figure 3:
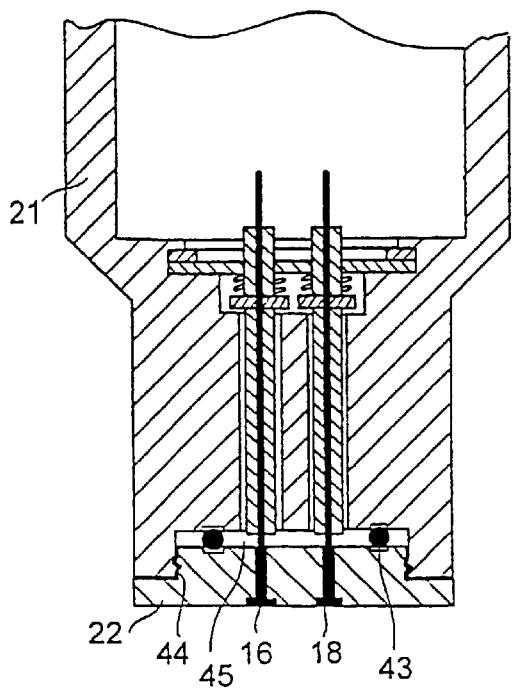
FIG. 3 is a cross sectional view of a second embodiment of a rotatable shaft and a replaceable measuring body according to the present invention.

A second embodiment of a measuring body 22 for attachment to the shaft 21 with threads is illustrated in FIG. 3. In this embodiment, an O-ring 43 is used as sealing only. Threads 44 are provided on the measuring body as well as on the inside of a recess 4S in the lower section of the shaft, thereby allowing the measuring body to be screwed onto the shaft. Similarly to the previously described embodiment, a ring-disk configuration having contact pins correspondingly situated always provides a proper electrical connection, while other positions of the measuring electrodes may require that the threaded connection between the measuring body and the shaft is formed with such a precision that the electrodes always ends in a position directly below their respective contact pins when the measuring body is screwed onto the shaft.

A measuring body according to this second embodiment has the advantage of being of small size and of a simple design, but the screwing operation during electrode replacement could be perceived as inconvenient.

A so-called bayonet-mount is also useful for attaching the measuring body to the shaft. The bayonet-mount, which may be designed in any suitable manner known by anyone skilled in the art, has the advantage to allow for high precision positioning of the measuring body with respect to the shaft, but it is typically rather expensive.

It should be noted that even in the case that the shaft is provided with numerous contact pins, measuring bodies having a fewer number of electrodes could be used as well, and vice verse, although the possibility to fully utilize all components is then lost.

Thus, the present invention provides a low cost measuring body having an arbitrary number of electrodes, and a shaft adapted thereto, for allowing a simple electrode replacement procedure.

What is claimed is:

1. A rotatable shaft of a measuring electrode assembly, the shaft having an upper end adapted to be supported for engagement with a drive means and a free lower end adapted for supporting at least one electrode that is immersed for rotation in an electrolytic fluid for amperometric determination of chemical components in the fluid, said shaft comprising:

at least one bore axially opening in an end face of the shaft lower end;

at least one contact pin slidably received in said at least one bore and electrically isolated from the shaft;

biasing means provided to act between the shaft and the contact pin in order to axially bias the contact pin towards the mouth of the bore;

fastening means for removably attaching a measuring body to the shaft such that an electrode, when supported on said measuring body, electrically connects said contact pin under a resilient pressure exerted from the biasing means.

2. The shaft of claim 1, wherein said at least one contact pin is axially biased to protrude externally with an end portion thereof below the end face of the shaft lower end, while an opposite end of the contact pin protrudes internally into a hollow space formed axially in the shaft, said internal end of the contact pin being connected to a collector connection supported on the shaft for electrically connecting at least one electrode of the measuring body with external equipment.

3. The shaft of claim 1, wherein said fastening means comprises a threaded engagement between the shaft and the measuring body, a separate seal shielding the contact area from exposure to the fluid.

4. The shaft of claim 3, wherein a disc-shaped measuring body is attached by being received in a recess formed in the end face of lower end of the shaft, at least one electrode extending through said disc such that an external end of the electrode is exposed to the fluid, and an opposite end of the electrode is in biasing contact with said at least one contact pin in the attached position of the measuring body.

5. The shaft of claim 1, wherein said fastening means comprises a frictional engagement between the shaft and the measured body, said frictional engagement being operative also for shielding the contact area from exposure to the fluid.

6. The shaft of claim 5, wherein a cup-shaped measuring body is attached concentrically about the periphery of the lower end of the shaft, said measuring body having a bottom portion and at least one electrode extending through said bottom portion such that an external end of the electrode is exposed to the fluid, and an opposite end of the electrode is in biasing contact with said at least one contact pin in the attached position of the measuring body.

7. The shaft of claim 1, wherein a first contact pin is centrally received in the shaft lower end and a second contact pin is eccentrically received in the shaft lower end, the shaft supporting a measuring body formed with a ring-disc electrode.

* * * * *